United States Patent
Lidolt et al.

(10) Patent No.: US 7,172,567 B2
(45) Date of Patent: Feb. 6, 2007

(54) ORTHOPEDIC AID WITH A LOCKING DEVICE

(75) Inventors: Klaus Lidolt, Duderstadt (DE); Matthias Schilling, Weissenborn-Lüderode (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 75 days.

(21) Appl. No.: 10/796,287

(22) Filed: Mar. 10, 2004

(65) Prior Publication Data
US 2005/0039762 A1   Feb. 24, 2005

(30) Foreign Application Priority Data
Mar. 12, 2003   (DE) ................. 103 11 187

(51) Int. Cl.
*A61F 5/00*   (2006.01)
*B61F 2/60*   (2006.01)
(52) U.S. Cl. ............... 602/23; 602/16; 623/30
(58) Field of Classification Search ............ 602/5, 602/20, 21, 23, 26, 12, 28, 29; 623/43, 30, 623/31; 340/573.1, 575; 482/1, 4, 6, 7, 482/903; 135/65, 72, 75
See application file for complete search history.

(56) References Cited

U.S. PATENT DOCUMENTS 5,052,375 A * 10/1991 Stark et al. ............. 601/34
5,103,807 A * 4/1992 Makaran ................. 601/40
6,436,058 B1 * 8/2002 Krahner et al. ......... 600/587
2004/0225242 A1 * 11/2004 Lidolt et al. ............ 602/16

FOREIGN PATENT DOCUMENTS

| DE | 2 314 510 | 10/1975 |
|---|---|---|
| DE | 200 05 559 | 7/2001 |
| DE | 201 19 621 | 3/2002 |
| EP | 0 141 640 | 5/1985 |
| EP | 0 380 060 | 8/1990 |
| GB | 1 386 942 | 3/1973 |
| GB | 2 280 609 | 2/1995 |
| WO | WO 00/79263 | 12/2000 |

OTHER PUBLICATIONS

XP000679254 H. Dietl et al. "Der Einsatz von Elektronik bei Prothesen zur Versorgung der unteren Extremitat" Med Orth. Tech. 117 (1997) pp. 31-35.
European Search Report dated Nov. 4, 2004.

* cited by examiner

*Primary Examiner*—Henry Bennett
*Assistant Examiner*—Shumaya B. Ali
(74) *Attorney, Agent, or Firm*—Whitham, Curtis, Christofferson & Cook, P.C.

(57) ABSTRACT

In an orthopedic aid with two parts (15, 16) which are movable relative to one another and with a locking device for locking the two parts (15, 16) in a predetermined relative position and for unlocking the parts (15, 16) in order to permit movement of the parts (15, 16) with respect to one another, the unlocking can be advantageously controlled by the fact that the locking device can be actuated electromechanically from a control module (8, 8'), and an actuating signal can be sent by wireless transmission from an actuating unit (9', 14) to the control module (8, 8').

10 Claims, 7 Drawing Sheets

Figure 4:
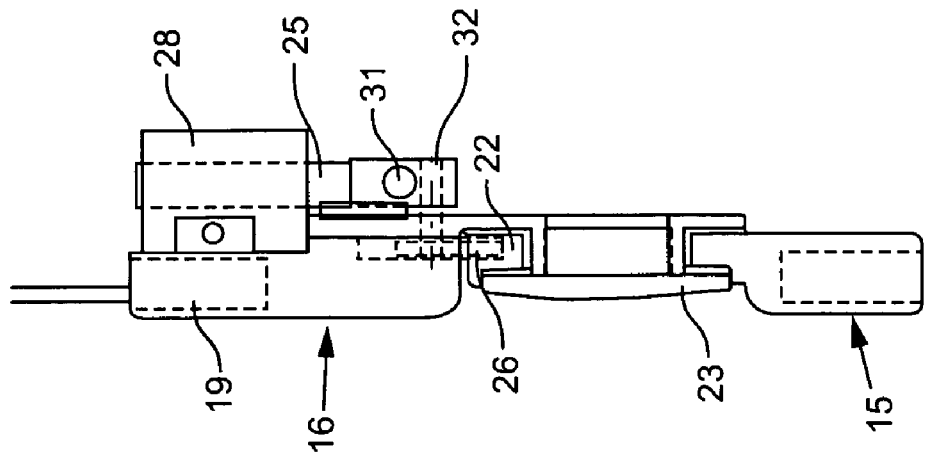

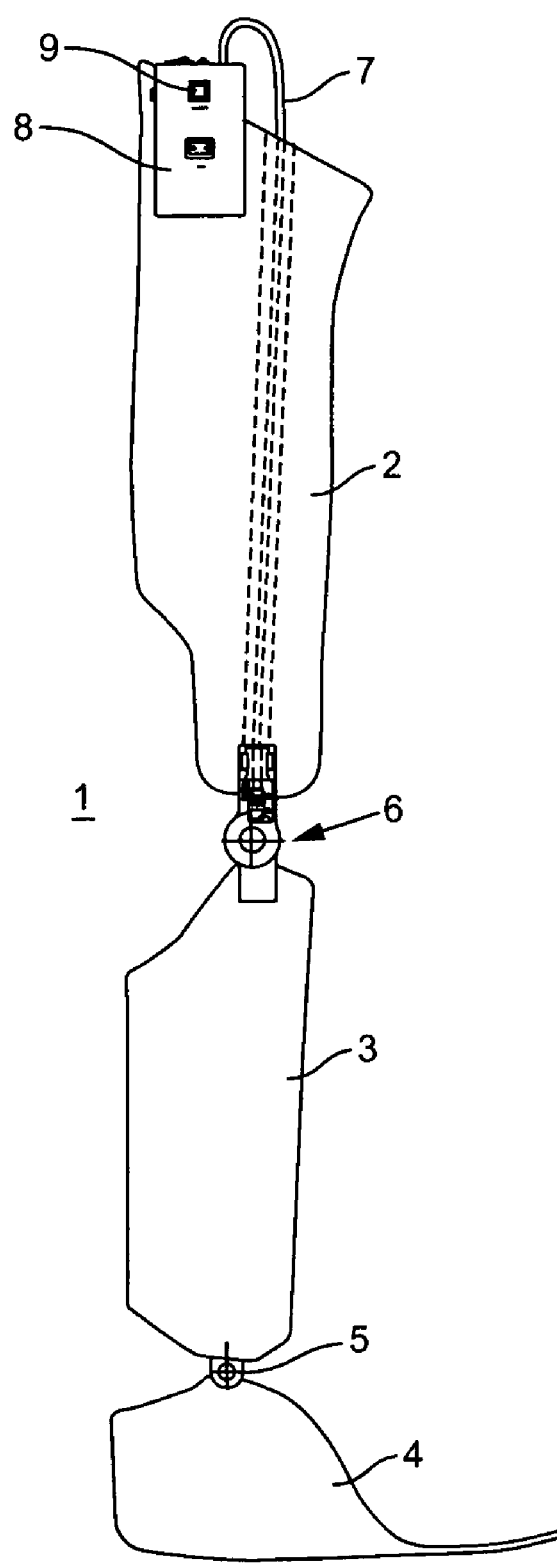
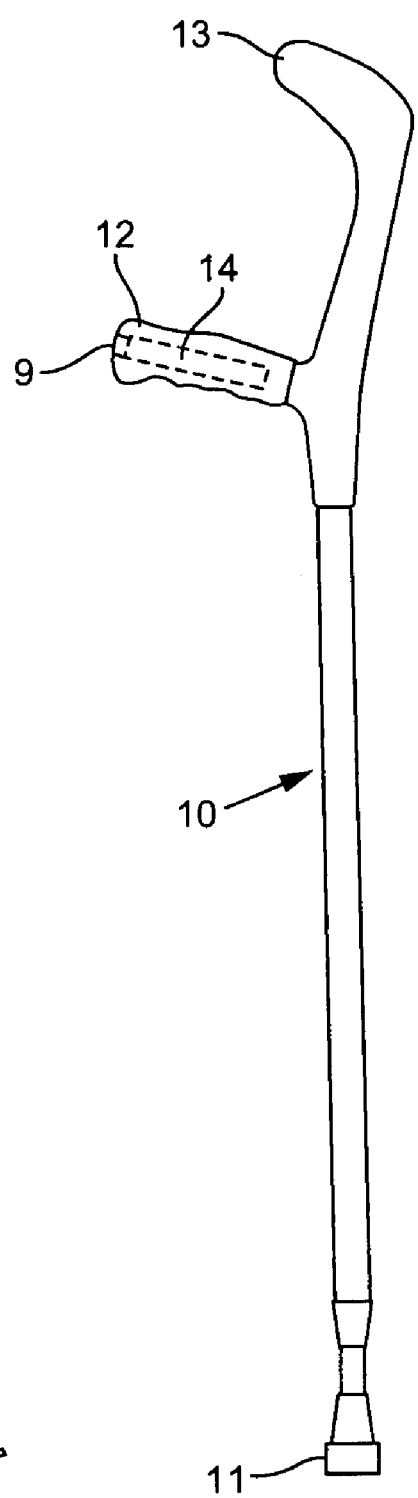
*Figure 1*
*Figure 2*

ORTHOPEDIC AID WITH A LOCKING DEVICE

The invention relates to an orthopedic aid with two parts which are movable relative to one another and with a locking device for locking the two parts in a predetermined relative position and for unlocking the parts in order to permit movement of the parts with respect to one another.

Orthopedic aids of this kind are used in many applications intended to provide compensation for temporary or permanent weaknesses of the human body and to enable functions that it would otherwise not be possible to perform. This is achieved by the orthopedic aid providing a supporting function in which, in a defined position of the parts of the aid, these parts are locked with respect to one another, and the locked position of the two parts with respect to one another corresponds to a position of use in which the patient concerned requires the supporting function afforded by the orthopedic aid. A preferred application of an orthopedic aid of this kind is in its design as an orthotic joint, where, for example, the parts of the orthotic joint connected to one another by a hinge can be locked in an extended position, for example in order to permit the function of a limb in the extended and locked position of the orthotic joint. To get to a rest position, the locking device has to be unlocked. In known orthotic knee joints, this is done, for example, by means of a Bowden cable with which the locking device can be unlocked, so that the knee joint can be flexed, for example in order to allow the patient to get to the seated position. Even if the Bowden cable is sited in a position in which it is easy to grasp, its actuation is nevertheless awkward and, for example in the case of an orthotic leg device, requires gripping the leg beneath or through the clothing, which many patients consider inconvenient.

The object of the present invention is therefore to design an orthopedic aid of the type mentioned at the outset in such a way that correct unlocking can be achieved in a simple manner.

To achieve this object, an orthopedic aid of the type mentioned at the outset is distinguished, according to the invention, by the fact that the locking device can be actuated electromechanically from a control module, and an actuating signal can be sent by wireless transmission from an actuating unit to the control module.

The orthopedic aid according to the invention thus provides for unlocking of the locking device by an electromechanical actuation triggered by a control module. The control module is provided with a signal receiver through which the control module can receive an actuating signal sent to it by wireless transmission and can convert this actuating signal into a switching signal for actuating the locking device.

In this way, an actuating unit for unlocking the orthopedic aid can be arranged at a convenient position and can, for example, be carried as a separate device in the clothing.

However, it is preferable to integrate the actuating unit into a walking aid. The actuating unit can in this case preferably be accommodated in a handgrip of the walking aid. It is expedient to arrange an actuating button on a free end face of the handgrip of the walking aid, so that the actuating button can be preferably actuated by the thumb of the hand holding the handgrip, without having to release the grasp on the handgrip of the walking aid.

The actuating unit can also be formed by a manual transmitter which can be carried separately and actuated. The manual transmitter is preferably designed in such a way that it can be fitted into a walking aid at the aforementioned positions and can be actuated when the walking aid is in use, the manual transmitter in this case preferably being accommodated in the handgrip of the walking aid and preferably being actuated by the thumb of the hand holding the handgrip.

In a further embodiment of the invention, an acknowledgement signal or warning signal can be transmitted from the control module to the actuating unit. In a preferred embodiment of the invention, the acknowledgement signal can indicate that, after an unlocking of the orthopedic aid, the latter has returned to the correctly locked position. This is important in particular for orthotic leg devices whose function it is to be used for walking in an extended position of the knee joint. The transmitted acknowledgement signal or warning signal can be used to trigger signaling arrangements of the actuating unit, for example visual and/or acoustic signal display arrangements and/or a vibrator.

For the actuating unit integrated in the handgrip of the walking aid, the arrangement of the vibrator in the handgrip of the walking aid is particularly expedient.

Figure 3:
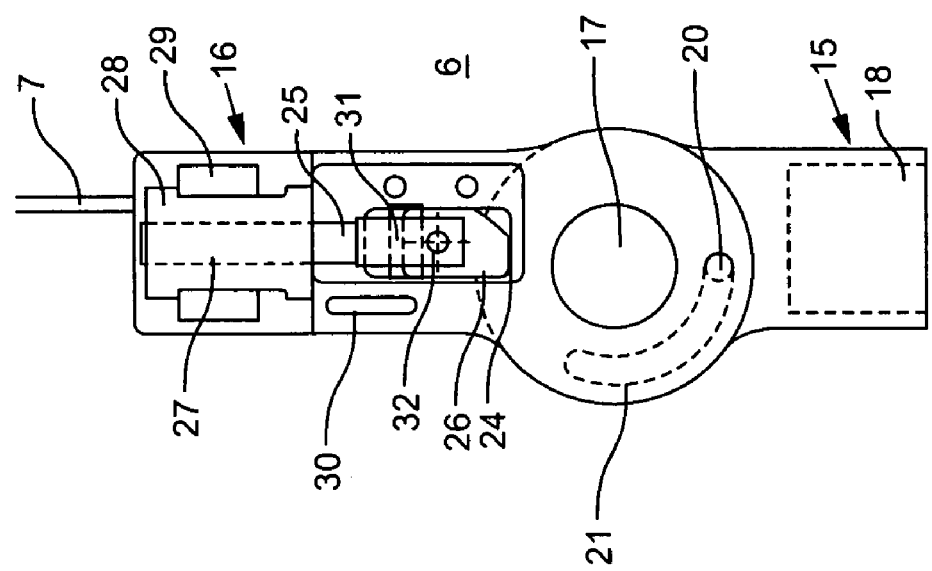
Figure 6:
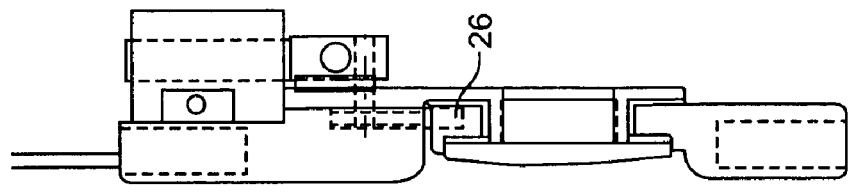
Figure 5:
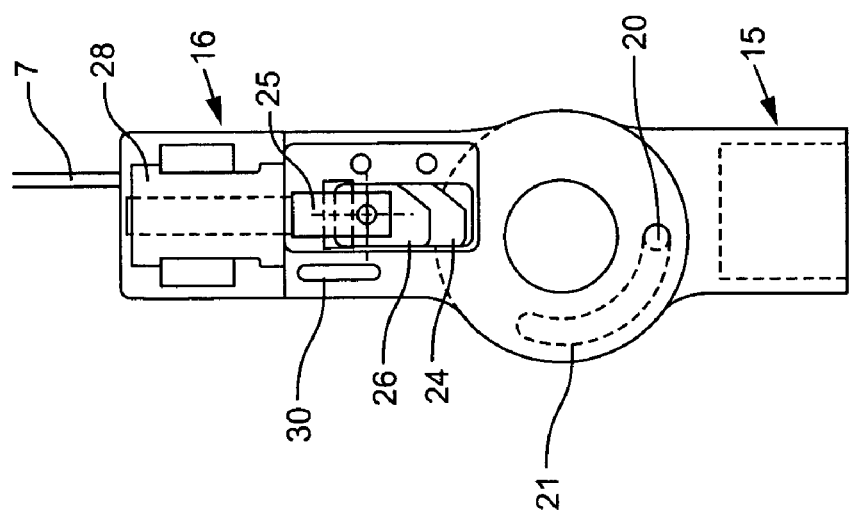
Figure 7:
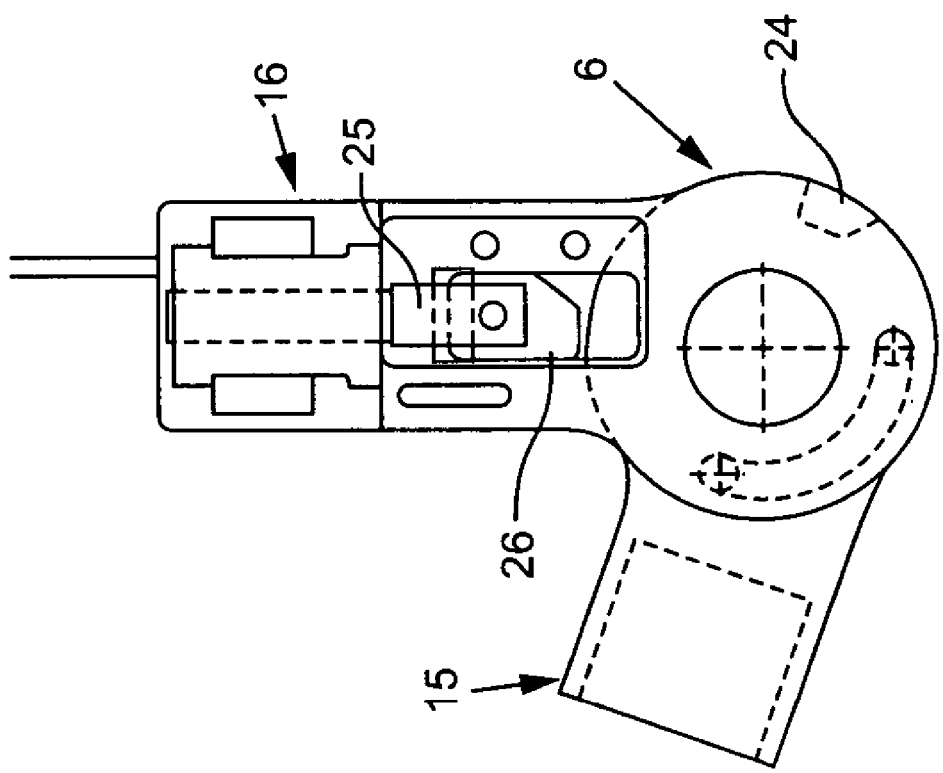
Figure 8:
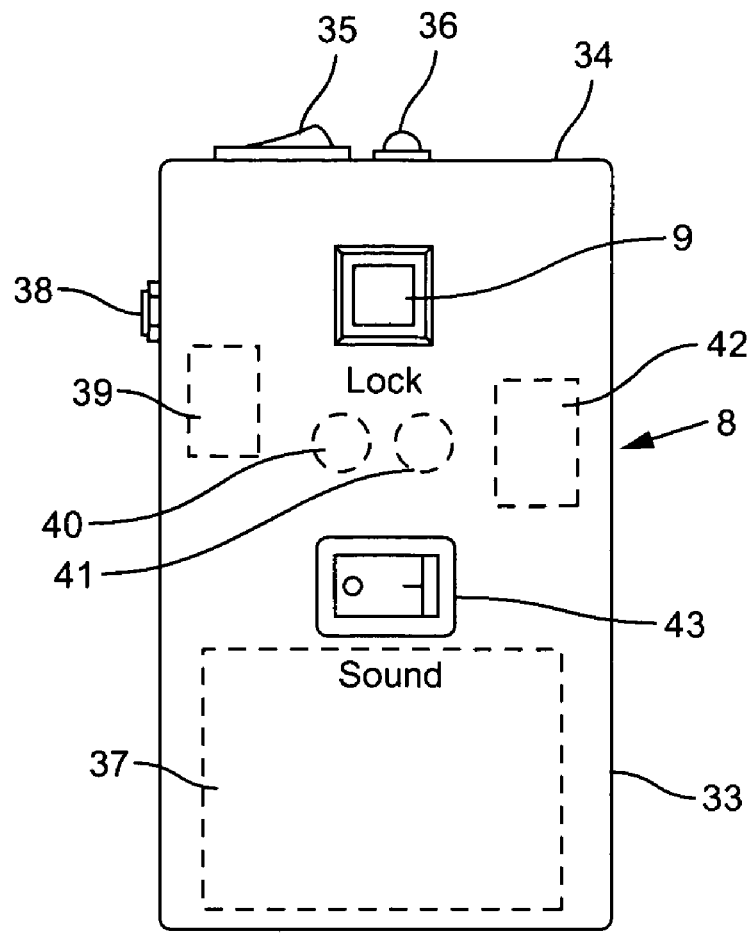
Figure 9:
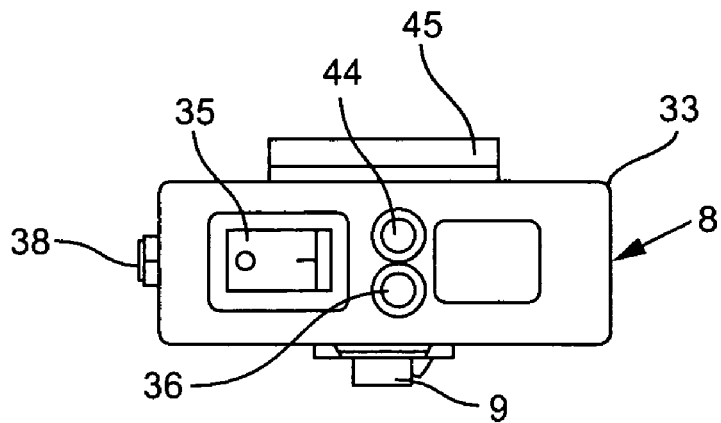
Figure 10:
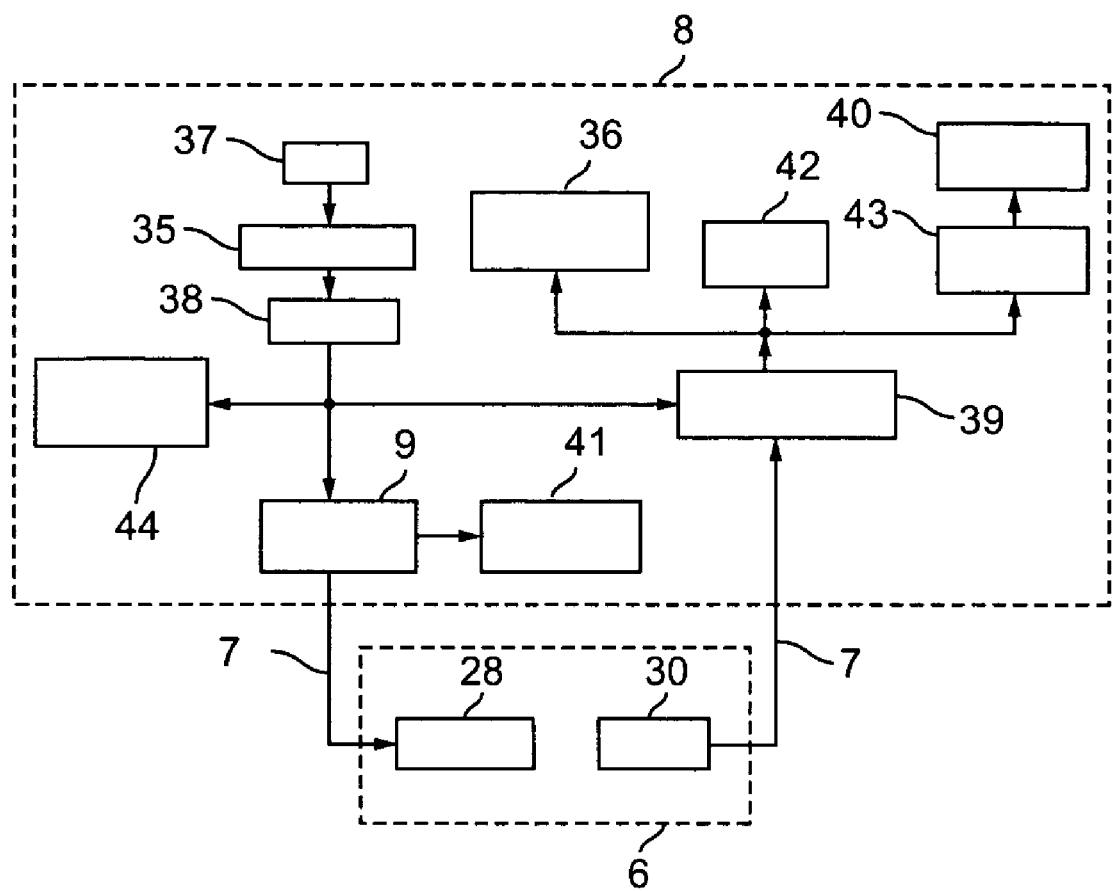
Figure 11:
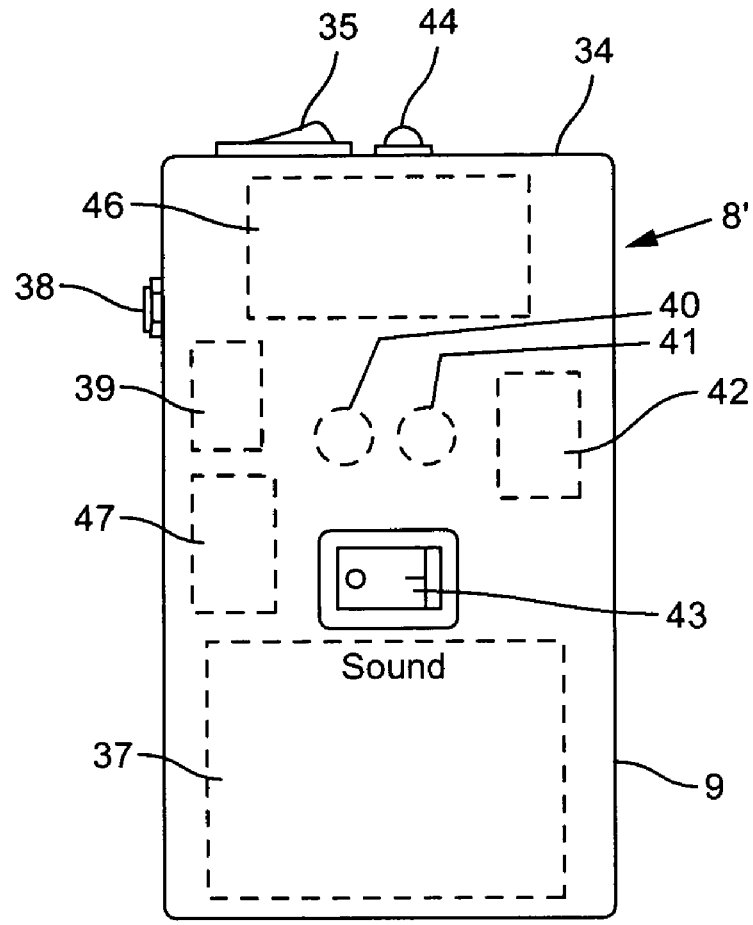
Figure 12:
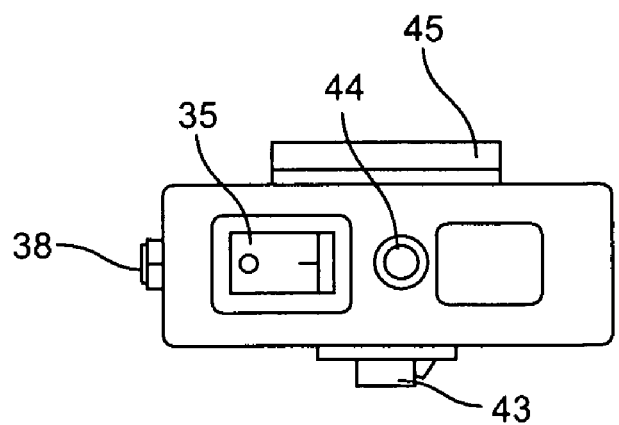

The invention is explained in greater detail below with reference to an illustrative embodiment shown in the drawing, in which:

FIG. 1 shows a side view of an orthotic leg device according to one embodiment of the invention, FIG. 2 shows a walking aid in the form of a crutch belonging to the orthotic leg device according to FIG. 1, FIG. 3 is a detail of a hinge of the orthotic device according to FIG. 1, shown in a side view and in the locked state, FIG. 4 shows the hinge according to FIG. 3 in a view from behind, FIG. 5 shows the view according to FIG. 3, with the hinge in the unlocked state, FIG. 6 shows the view according to FIG. 4, with the hinge in the unlocked state, FIG. 7 shows a side view of the hinge according to FIG. 5, in the flexed state, FIG. 8 shows a side view of a control module with an unlocking key, FIG. 9 shows a plan view of the control module according to FIG. 8, FIG. 10 shows a block diagram of the electrical parts of the orthotic leg device according to FIG. 1, equipped with a control module according to FIGS. 8 and 9, FIG. 11 shows a control module for the orthotic leg device according to FIG. 1, with wireless control, FIG. 12 shows a plan view of the control module according to FIG. 11.

The orthotic leg device 1 shown in FIG. 1 has a thigh shell 2, a below-knee shell 3 and a foot shell 4. The below-knee shell 3 and the foot shell 4 are connected to one another via a pivot hinge 5. Arranged between the thigh shell 2 and the below-knee shell 3 there is a lockable hinge 6 which is connected via a connection cable 7 to a control module 8 which can be attached on the top of the thigh shell 2.

Flat stiffening rods (not shown in FIG. 1) can be inserted into the hinge 6 and can be connected to the thigh shell 2 and below-knee shell 3.

The hinge 6 can be locked in the extended position shown in FIG. 1 and can be unlocked by means of an unlocking key 9 on the control module 8.

FIG. 2 shows a walking aid 10 in the form of a bar-shaped crutch which, at the bottom end, has a rubber part 11 for placing on the ground and, at the upper end, has a handgrip 12 and a forearm support 13. A trigger switch 9' is integrated into the handgrip 12 and can be actuated from the end face of the handgrip 12, preferably by thumb, and acts on a transmitter 14 which then can send an actuating signal for the control module 8. The control module 8 is in this case set up for radio reception.

The structure of the hinge 6 is shown in greater detail in FIGS. 3 through 7. The hinge 6 consists of two hinge parts 15, 16 which are pivotably connected to one another via the pivot 17.

The part 15 is designed as the lower part of the hinge, with a downwardly open receiving compartment 18 for a flat stiffening rod, which is connected to the below-knee shell 3. Correspondingly, the part 16 has an upwardly open receiving compartment 19 for receiving a stiffening rod for the thigh shell 2.

The lower part 15 of the hinge is provided with a guide pin 20 which can be moved in a guide groove 21 forming approximately a quarter of a circle and thus forms abutments for the extended position according to FIG. 3 and for a flexed position of the hinge 6 according to FIG. 7.

In the area of the pivot 17, the lower part 15 and upper part 16 of the hinge both form circular, eye-shaped end portions 22, 23 which are fitted in one another to form the pivot 17. The end portion 22 of the lower part 15 of the hinge is provided with a radial recess 24 into which a locking pin 25 engages with a lower end 26 shaped to match the recess 24, in order to lock the lower part 15 and upper part 16 of the hinge together in the extended position shown in FIGS. 3 and 4. At its upper end, the locking pin 25 merges into a cylindrical core 27 which is axially movable in the interior of an electrical coil 28. The electrical coil 28 is fixed in a mounting 29 in the upper part of the hinge. The position of the locking pin 25 can be detected by means of a sensor 30 arranged together with the locking pin 25 in the upper part 16 of the hinge and extending parallel to said locking pin 25. A permanent magnet 31 connected to the locking pin 25 and interacting with the sensor 30 extends transversely with respect to the locking pin 27 and its magnetic field can be detected by the sensor 30, which can be a Hall sensor. In the locked position shown in FIG. 3, the sensor 30 does not detect any magnetic field of the permanent magnet 31. If the locking pin 25 moves upward because it is drawn, by a flow of current, through the coil 28 and into the interior of the latter, the field of the permanent magnet 31 reaches the area of the sensor 30, which thus detects the unlocked state. Both the current for the coil 28 and the output signal of the sensor 30 are transmitted from/to the control module 8 via the connection cable 7.

FIG. 4 illustrates that the endpiece 26 of the locking pin 25 can be shifted axially sideways and is connected to the locking pin 25 via a connecting pin 32.

FIGS. 5 and 6 show the hinge 6 in the unlocked state. Current flows through the coil 28 via the connection cable 7, and the coil 28 acts as electromagnet for the locking pin 25 which is drawn into the interior of the coil 28 (upward as shown in the drawing) and pulls the end 26 connected to it from the associated recess 24, so that the lower part 15 of the hinge is now pivotable relative to the upper part 16 of the hinge, specifically within the guide 20, 21 defined by the guide pin 20 and the guide groove 21.

FIG. 7 shows the flexed end position of the hinge 6, as is adopted when the user sits down. The end 26 of the locking pin 25 slides on the cylindrical peripheral surface of the end portion 22 of the lower part 15 of the hinge. If the user moves from the flexed state according to FIG. 7 to the extended state according to FIGS. 3 through 6, the lower end 26 of the locking pin 15 slides, under the effect of gravity, on the peripheral surface of the end portion 22 until the lower end 26 drops into the recess 24 in the fully extended position and actuates the lock according to FIGS. 3 and 4.

The control module 8 illustrated in FIGS. 8 and 9 has the key 9, for unlocking the hinge 6, at a position convenient to reach. The control module is provided with a rectangular, flat housing 33 on whose narrow top face 34 there is a main switch 35 with a warning light 36. The housing 33 contains, on the underside, a battery 37, which can be recharged via a charge socket 38 arranged on a narrow side wall. The control module 8 further includes a short-time control 39 and two sound generators 40, 41 and a vibrator 42. The sound generators 40, 41 can be switched off via a switch 43 in order to suppress an acoustic signal in certain situations where the latter would be undesirable.

FIG. 9 shows that the top face 34 of the housing 33 is provided with a further control light 44 indicating the state of charging of the battery 37. The housing 33 is moreover provided with a clip bracket 45 with which it can be clipped onto the top edge of the thigh shell 2.

The block diagram in FIG. 10 shows the functional circuitry in the control module 8 and the signals transmitted to the hinge 6 via the connection cable 7.

The battery 37 is connected via the main switch 35 to the charge socket 38 and to the key 9 for unlocking the hinge 6. When the key 9 is actuated, the sound generator 41 is triggered and emits a warning sound for unlocking. With the main switch 35 switched on, the state of charging of the battery 37 is indicated by the control light 44; for example, the control light 44 does not light if the state of charging of the battery 37 is sufficient. By actuating the key 9, a current is conveyed via the connection cable 7 into the coil 28 in the hinge 6, as a result of which the hinge is unlocked.

If the sensor 30 of the hinge 6 detects that the locking pin 25 has dropped back into the locked position, this output signal of the sensor 30 is transmitted via the connection cable 7 to the control module 8 and there, via the short-time control 39, emits acknowledgement signals, namely by the control light 36 lighting up via the short-time control 39, actuation of the vibrator 42, and actuation of the sound generator 40, unless the latter has been switched off via the switch 43.

FIGS. 11 and 12 show the control module 8' for radio reception of an actuating signal triggered by the transmitter 14 of the walking aid 10 and is therefore additionally provided with a radio receiver 46 and a switching relay 47 instead of with the switch 9. Of course, it is also possible to provide, in addition to the radio receiver 46 and the switching relay 47, the possibility of unlocking via the key 9 in the control module 8, 8'.

In the embodiment shown in FIGS. 11 and 12, the fact that the switch 9 is omitted also means that the corresponding control light 36 is dispensed with, so that only the control light 44 for the state of charging of the battery 37 is now located on the top face 34 of the housing 9.

Otherwise, the control module 8' is identical to the control module 8.

The invention claimed is:

1. An orthopedic aid, comprising:
   two parts of an orthopedic joint which are movable relative to one another;
   a walking aid, having a handgrip structure having a grip surface that is readily gripped by a person, and a ground contact surface, constructed and arranged such that the person can grip the grip surface and, while maintaining the grip, place the ground contact surface in contact with the ground, that is separate from said orthopedic joint;

an actuating unit integrated into said walking aid, for sending an actuating signal by wireless transmission;

a locking device, movable between a lock position and an unlock position, wherein in said lock position it engages said orthopedic joint so as to lock the two parts in a predetermined relative position and in said unlock position it permits movement of the two parts with respect to one another; and a control unit constructed and arranged to receive said actuating signal and, in response, electromechanically actuate said locking device to at least one of said lock position and unlock position.

2. The orthopedic aid of claim 1, wherein the actuating unit is arranged and mounted in said handgrip structure of the walking aid.

3. The orthopedic aid of claim 2, further comprising an actuating button arranged on or proximal to said handgrip surface.

4. The orthopedic aid of claim 1, wherein the actuating unit includes a manually selectably activated transmitter.

5. The orthopedic aid of claim 1, wherein the control module is constructed and arranged to detect completion of a movement of said locking device from said unlock position to said lock position and, in response to said detecting, to transmit an acknowledgment signal to the actuating unit.

6. The orthopedic aid of claim 5, wherein the actuating unit includes one or more of a visual display,
an acoustic signal arrangement, and
a vibrator, wherein one or more of said visual display, acoustic signal arrangement, or said vibrator is activated by said acknowledgment signal transmitted by said control module.

7. The orthopedic aid of claim 6, wherein the vibrator is arranged and mounted in said handgrip structure of the walking aid.

8. The orthopedic aid of 1, wherein the control module is constructed and arranged to detect completion of a movement of said locking device from said lock position to said unlock position and, in response to said detecting, to transmit a warning signal to the actuating unit.

9. The orthopedic aid of claim 8, wherein the actuating unit includes one or more of a visual display,
an acoustic signal arrangement, and
a vibrator, wherein one or more of said visual display, acoustic signal arrangement, or said vibrator is activated by said warning signal transmitted by said control module.

10. The orthopedic aid of claim 9, wherein the vibrator is arranged and mounted in said handgrip structure of the walking aid.

* * * * *